(12) United States Patent
Green

(10) Patent No.: US 12,350,188 B2
(45) Date of Patent: Jul. 8, 2025

(54) DRAIN ASEMBLY FOR ELIMINATION OF URINE WASTE FROM AN OSTOMY BAG

(71) Applicant: GV SOLUTIONS LLC, Camp Hill, PA (US)

(72) Inventor: Marion R. Green, Camp Hill, PA (US)

(73) Assignee: Solutions LLC, Camp Hill, PA (US)

( * ) Notice: Subject to any disclaimer, the term of this patent is extended or adjusted under 35 U.S.C. 154(b) by 0 days.

(21) Appl. No.: 18/627,724

(22) Filed: Apr. 5, 2024

(65) Prior Publication Data
US 2024/0245542 A1    Jul. 25, 2024

Related U.S. Application Data

(63) Continuation of application No. 18/311,369, filed on May 3, 2023, now Pat. No. 11,951,028, which is a continuation of application No. 17/968,315, filed on Oct. 18, 2022, now Pat. No. 11,701,249.

(60) Provisional application No. 63/273,238, filed on Oct. 29, 2021.

(51) Int. Cl.
*A61F 5/445* (2006.01)
*A61F 5/44* (2006.01)

(52) U.S. Cl.
CPC ............ *A61F 5/4405* (2013.01); *A61F 5/445* (2013.01); *A61F 5/4404* (2013.01)

(58) Field of Classification Search
CPC ....... A61F 5/445; A61F 5/4406; A61F 5/4404
See application file for complete search history.

(56) References Cited

U.S. PATENT DOCUMENTS

| | | | | |
|---|---|---|---|---|
| 3,415,299 A | * | 12/1968 | Hinman, Jr. | A61F 5/44 604/326 |
| 3,823,716 A | * | 7/1974 | Hale | A61F 5/44 604/335 |
| 4,084,590 A | * | 4/1978 | Caraway | A61F 5/445 604/350 |
| 4,238,059 A | * | 12/1980 | Caraway | A61F 5/4405 285/332 |
| 4,254,771 A | * | 3/1981 | Vidal | A61F 5/441 604/325 |
| 4,280,498 A | * | 7/1981 | Jensen | A61F 5/4405 604/323 |
| 4,300,560 A | * | 11/1981 | Steer | A61F 5/445 222/530 |
| 4,540,156 A | * | 9/1985 | Cross | F16K 31/602 604/350 |
| 4,573,983 A | * | 3/1986 | Annis | A61F 5/441 600/580 |

(Continued)

FOREIGN PATENT DOCUMENTS

| | | |
|---|---|---|
| AU | 6343680 A | 4/1981 |
| CA | 1160126 A | 1/1984 |

(Continued)

*Primary Examiner* — Guy K Townsend
(74) *Attorney, Agent, or Firm* — Saxton & Stump, LLC

(57) ABSTRACT

A drain assembly for use with an ostomy bag and an ostomy bag arrangement utilizing a drain assembly to drain urine. The drain assembly includes a connector configured to attach to the ostomy bag. The drain assembly is configured to permit an ostomy bag wearer to position the discharge valve into a discharge position outside of the ostomy bag wearer's clothing for discharge of urine waste from the ostomy bag.

20 Claims, 6 Drawing Sheets

(56) References Cited

U.S. PATENT DOCUMENTS

| | | | | |
|---|---|---|---|---|
| 4,592,750 A * | 6/1986 | Kay | ............... | A61F 5/4407 604/277 |
| 4,634,437 A * | 1/1987 | Lowthian | ............... | A61F 5/44 600/580 |
| D300,361 S * | 3/1989 | Tokarz | ............... | D24/129 |
| 4,889,533 A | 12/1989 | Beecher | | |
| 4,909,478 A * | 3/1990 | Steer | ............... | F16K 5/0414 604/323 |
| 5,098,420 A * | 3/1992 | Iacone | ............... | A61F 5/448 604/338 |
| 5,299,777 A * | 4/1994 | Milstead | ............... | F01M 11/0408 251/291 |
| 6,132,408 A * | 10/2000 | Lutz | ............... | A61F 5/4407 604/335 |
| 6,224,581 B1 * | 5/2001 | Withers | ............... | A61F 5/445 604/332 |
| 6,726,667 B2 * | 4/2004 | Leise, Jr | ............... | A61F 5/445 604/335 |
| 7,008,407 B1 * | 3/2006 | Kamp | ............... | A61F 5/4405 604/327 |
| 7,223,260 B2 | 5/2007 | Hansen et al. | | |
| 7,476,220 B2 * | 1/2009 | Lillegaard | ............... | A61F 5/4404 604/338 |
| 7,879,015 B2 | 2/2011 | Villefrance et al. | | |
| D649,241 S * | 11/2011 | Kunishige | ............... | D24/129 |
| 8,292,858 B2 * | 10/2012 | Burgess | ............... | A61F 5/4405 604/326 |
| 8,882,732 B2 * | 11/2014 | March | ............... | A61F 5/445 604/332 |
| 9,333,110 B2 * | 5/2016 | March | ............... | A61F 5/445 |
| 10,251,770 B2 * | 4/2019 | Chang | ............... | A61F 5/445 |
| D910,170 S | 2/2021 | Scalise et al. | | |
| 11,000,400 B2 | 5/2021 | Grum-Schwensen et al. | | |
| 11,065,144 B2 * | 7/2021 | Nielsen | ............... | A61F 5/4407 |
| D978,345 S * | 2/2023 | Green | ............... | D24/129 |
| 11,701,249 B2 * | 7/2023 | Green | ............... | A61F 5/445 604/335 |
| 11,951,028 B2 * | 4/2024 | Green | ............... | A61F 5/4405 |
| 12,290,657 B1 * | 5/2025 | Plocher | ............... | A61F 5/445 |
| 2005/0273065 A1 * | 12/2005 | Lillegaard | ............... | A61F 5/4405 604/332 |
| 2006/0155252 A1 | 7/2006 | Walker et al. | | |
| 2009/0163883 A1 * | 6/2009 | Christensen | ............... | A61F 5/441 604/328 |
| 2010/0298789 A1 | 11/2010 | Santimaw | | |
| 2012/0130329 A1 * | 5/2012 | March | ............... | F16K 3/24 604/332 |
| 2013/0338616 A1 * | 12/2013 | Galindo | ............... | A61F 5/4405 604/335 |
| 2015/0025483 A1 * | 1/2015 | March | ............... | A61F 5/4405 604/318 |
| 2015/0190272 A1 * | 7/2015 | Chang | ............... | A61F 5/445 604/335 |
| 2019/0231582 A1 | 8/2019 | Kobke | | |
| 2020/0046543 A1 * | 2/2020 | Scalise | ............... | A61F 5/445 |
| 2021/0022911 A1 * | 1/2021 | Scalise | ............... | A61F 5/448 |
| 2021/0251795 A1 * | 8/2021 | Holroyd | ............... | A61F 5/4405 |
| 2021/0251796 A1 * | 8/2021 | Holroyd | ............... | A61F 5/4405 |
| 2021/0251797 A1 * | 8/2021 | Holroyd | ............... | A61F 5/4405 |
| 2021/0259874 A1 * | 8/2021 | Oellgaard | ............... | A61F 5/44 |
| 2022/0142808 A1 | 5/2022 | Weinberg et al. | | |
| 2023/0138034 A1 * | 5/2023 | Green | ............... | A61F 5/4404 604/335 |
| 2023/0270581 A1 * | 8/2023 | Green | ............... | A61F 5/445 604/323 |
| 2024/0245542 A1 * | 7/2024 | Green | ............... | A61F 5/445 |

FOREIGN PATENT DOCUMENTS

| | | |
|---|---|---|
| CA | 3049266 A | 7/2018 |
| CN | 1265772 C | 7/2006 |
| CN | 1311791 C | 4/2007 |
| CN | 106535836 B | 12/2018 |
| EP | 1221916 B1 | 8/2004 |
| EP | 2642956 B1 | 7/2017 |
| GB | 2593013 A | 9/2021 |
| JP | 5261363 B2 | 5/2013 |
| WO | 2016008495 A1 | 1/2016 |
| WO | 2019221830 A1 | 11/2019 |
| WO | 2021165675 A1 | 8/2021 |
| WO | 2021165676 A1 | 8/2021 |

* cited by examiner

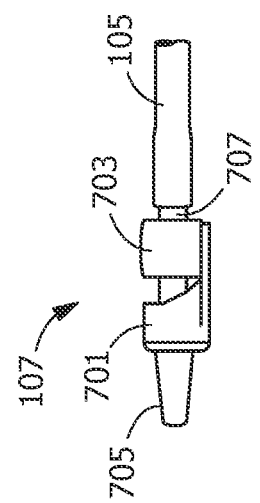
FIG. 7
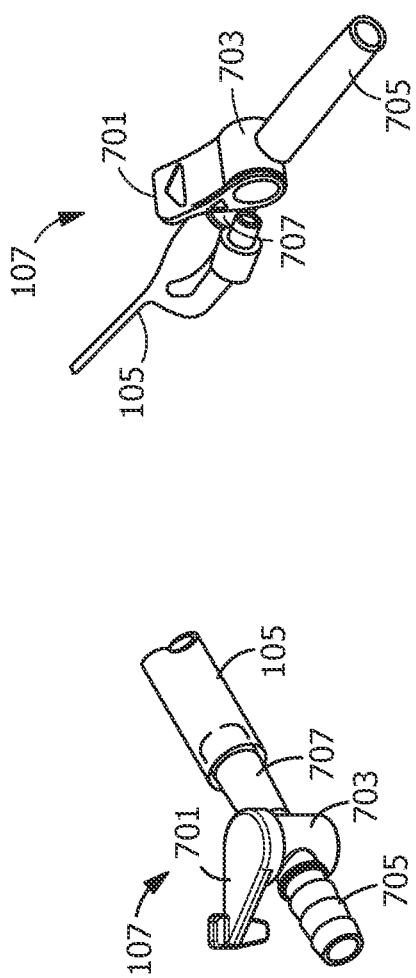
FIG. 8
FIG. 9
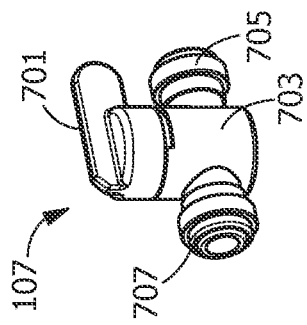
FIG. 10
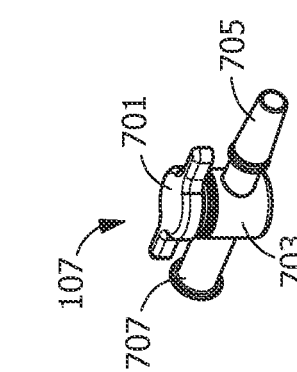
FIG. 11
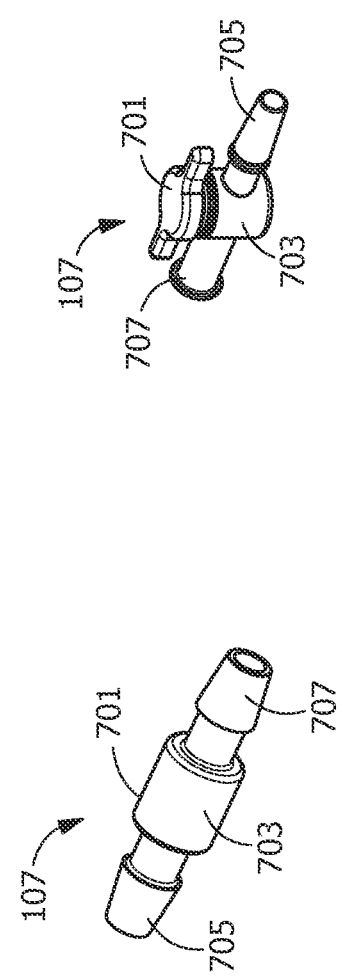
FIG. 12

DRAIN ASEMBLY FOR ELIMINATION OF URINE WASTE FROM AN OSTOMY BAG

CROSS-REFERENCE TO RELATED APPLICATIONS

This application claims priority and benefit of to U.S. Ser. No. 18/311,369, entitled "METHOD FOR ASSEMBLING A DRAIN ASSEMBLY AND METHOD FOR ELIMINATION OF URINE WASTE FROM AN OSTOMY BAG", filed May 3, 2023, which claims priority and the benefit of U.S. patent application Ser. No. 17/968,315, entitled "DRAIN ASSEMBLY FOR ELIMINATION OF URINE WASTE FROM AN OSTOMY BAG", filed Oct. 18, 2022, now U.S. Pat. No. 11,701,249, which claims priority and benefit of to provisional patent application U.S. Ser. No. 63/273,238, entitled "BOBTAIL TUBE EXTENSION WITH VALVES FOR ELIMINATION OF URINE WASTE FROM AN OSTOMY BAG" filed Oct. 29, 2021, each of which are incorporated by reference herein in their entirety.

FIELD OF THE INVENTION

The present disclosure is generally directed to medical devices. In particular, the present disclosure is directed to drain assemblies and ostomy bag arrangements for elimination of urine waste from an ostomy bag.

BACKGROUND OF THE INVENTION

Ostomy bags or pouches are used to trap urine draining through a stoma on the stomach wall. Current ostomy bags are drained in various ways. Some bags have a long pin like device to pinch the bottom of the bag closed. Other ostomy bags have valves that are either openings which can be plugged or a valve with turns open or closed.

All known ostomy bags provide a cumbersome way to be emptied. The ostomy bag must be pulled out from clothing to be emptied while standing or sitting. This requires that the bag be held by the wearer or caregiver as the pin or plug is removed and/or the valve opened to allow the urine to drain. The bags empty the same way for men or women. Draining the bag is done through an opening at the bottom of the bag which means the opening must be held in while aiming for the disposal location. The current process to empty all ostomy bags is using a very short valve or plug at the bottom of the bag. These valves or plugs only extend for about ½ inch. This manner of draining provides an undesirable lack of accuracy resulting in spillage and mess.

What is needed are a drain assembly, ostomy bag arrangement and method for draining urine that is convenient, discreet and more accurate than existing ostomy bags. Other features and advantages will be made apparent from the present specification. The teachings disclosed extend to those embodiments that fall within the scope of the claims, regardless of whether they accomplish one or more of the aforementioned needs.

SUMMARY OF THE INVENTION

The present disclosure is directed to a drain assembly and ostomy bag arrangement that allows for male and female wearers of ostomy bags to discreetly and more accurately empty bags of urine waste. For example, the ostomy bag arrangement according to the present disclosure allows male wearers to use the device while at a urinal by simply pulling the flexible conduit with the discharge valve out and opening the valve. Likewise, the drain assembly according to the present disclosure allows a woman to stand facing the toilet and draining the ostomy bag. The longer drain assembly helps with handling the various clothing items. The drain assembly also allows a man or woman to easily sit and drain the ostomy bag into the toilet. It affords privacy and accuracy for all users.

According to an embodiment of the present disclosure, a drain assembly for use with an ostomy bag is provided. The drain assembly includes a connector configured to attach to the ostomy bag. A flexible conduit extends from the connector. A discharge valve is positioned at a distal end of the flexible conduit from the connector. The flexible conduit is of a sufficient length and sufficient flexibility to permit an ostomy bag wearer to position the discharge valve into a discharge position outside of the ostomy bag wearer's clothing for discharge of urine waste from the ostomy bag.

According to an embodiment of the present disclosure, an ostomy bag arrangement for elimination of waste urine from an ostomy bag is provided. The ostomy bag arrangement includes an ostomy bag for receiving waste urine from an ostomy bag wearer. The ostomy bag arrangement also includes a drain assembly detachably engaged to the ostomy bag. The drain assembly includes a connector configured to attach to the ostomy bag. A flexible conduit extends from the connector. A discharge valve is positioned at a distal end of the flexible conduit from the connector. The flexible conduit is of a sufficient length and sufficient flexibility to permit an ostomy bag wearer to position the discharge valve into a discharge position outside of the ostomy bag wearer's clothing for discharge of urine waste from the ostomy bag.

According to an embodiment of the present disclosure, a kit for assembly of a drain assembly for attachment to an ostomy bag is provided. The kit includes a plurality of flexible conduits, each having a configuration that permits attachment to a connector and a discharge valve at distal ends of the flexible conduit. The connector is configured to attach to the ostomy bag. The discharge valve is configured to permit connection to the flexible conduit at a distal end from the connector. The flexible conduit, when assembled to the connector and the discharge valve, includes sufficient length and sufficient flexibility to permit an ostomy bag wearer to position the discharge valve into a discharge position outside of the ostomy bag wearer's clothing for discharge of urine waste from the ostomy bag.

Other features and advantages of the present invention will be apparent from the following more detailed description of the preferred embodiment, taken in conjunction with the accompanying drawings which illustrate, by way of example, the principles of the invention.

BRIEF DESCRIPTION OF DRAWINGS

FIG. 7 shows a discharge valve for use with a drain assembly according to an embodiment of the present disclosure.

FIG. 8 shows an alternate discharge valve for use with a drain assembly according to an embodiment of the present disclosure.

FIG. 9 shows an alternate discharge valve for use with a drain assembly according to an embodiment of the present disclosure.

FIG. 10 shows an alternate discharge valve for use with a drain assembly according to an embodiment of the present disclosure.

FIG. 11 shows an alternate discharge valve for use with a drain assembly according to an embodiment of the present disclosure.

FIG. 12 shows an alternate discharge valve for use with a drain assembly according to an embodiment of the present disclosure.

Wherever possible, the same reference numbers will be used throughout the drawings to represent the same parts.

DETAILED DESCRIPTION OF THE INVENTION

Disclosed herein is a new and useful device and system that affords an ostomy bag wearer, such as a person that has had a urostomy, both greater discreet drainage of the urine waste from an ostomy bag and greater control of the flow of the urine waste. For example, the ostomy bag arrangement according to the present disclosure affords the male wearer a sense of normalcy while using a urinal. In addition, the ostomy bag arrangement according to the present disclosure affords peace of mind to both male and female users of ostomy bags that an ostomy bag can be conveniently, accurately, and discreetly emptied either into a urinal, toilet or other suitable waste receptacle.

By use of the drain assembly according to the present disclosure, a male can wear an ostomy bag having a drain assembly according to the present disclosure attached thereto and empty the ostomy bag while discreetly standing at a urinal without having to extract the ostomy bag from the wearer's clothing. Likewise, by use of the drain assembly according to the present disclosure male or female has greater control of the flow and direction of urine emptying a bag while seated on a toilet. An ostomy bag wearer may drain an ostomy bag with a greater control of direction of the emptying flow of urine by directing the end of the drain assembly into a urinal, much like the natural way to void the bladder. Alternatively, the drain assembly may be positioned with the ostomy bag wearer in a seated position with the discharge valve below the toilet seat, which allows males or females to take advantage of the convenient and discreet draining of the ostomy bag. In another embodiment, the ostomy bag may be emptied into any convenient waste receptacle, such as a bottle or other receptacle, for example, when there is no restroom available, with the discharge vale being able to be directed into the waste receptacle. Further objects and advantages of the presently disclosed invention is to allow a way to provide a convenient and discreet way to empty an ostomy bag in public.

Figure 1:
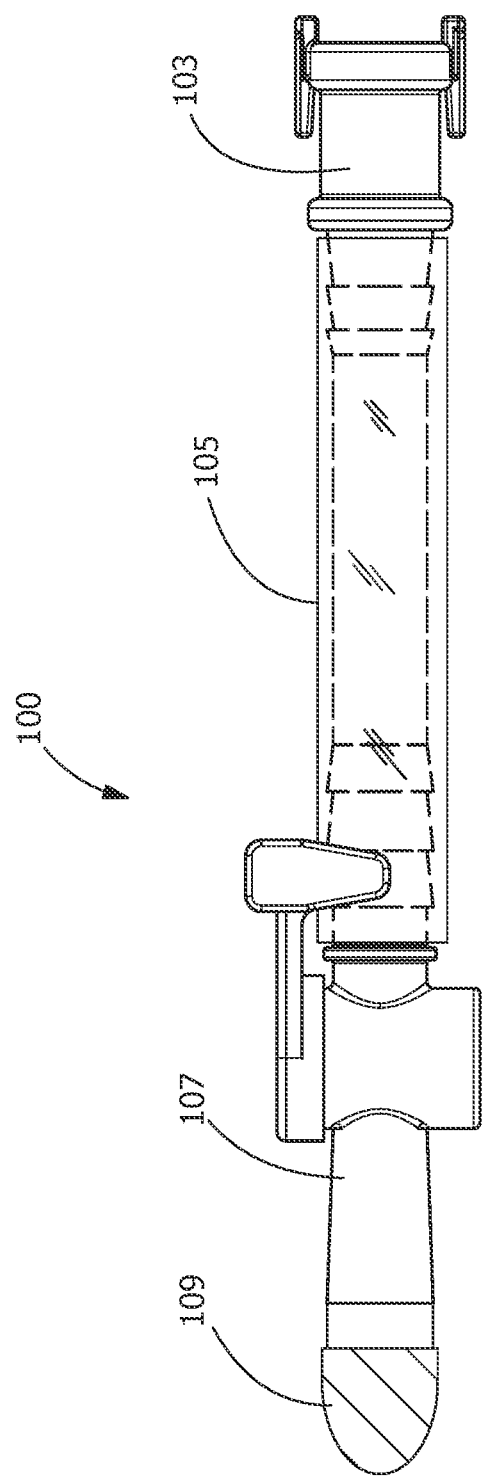
FIG. 1 schematically illustrates a drain assembly according to an embodiment of the present disclosure.
Figure 2:
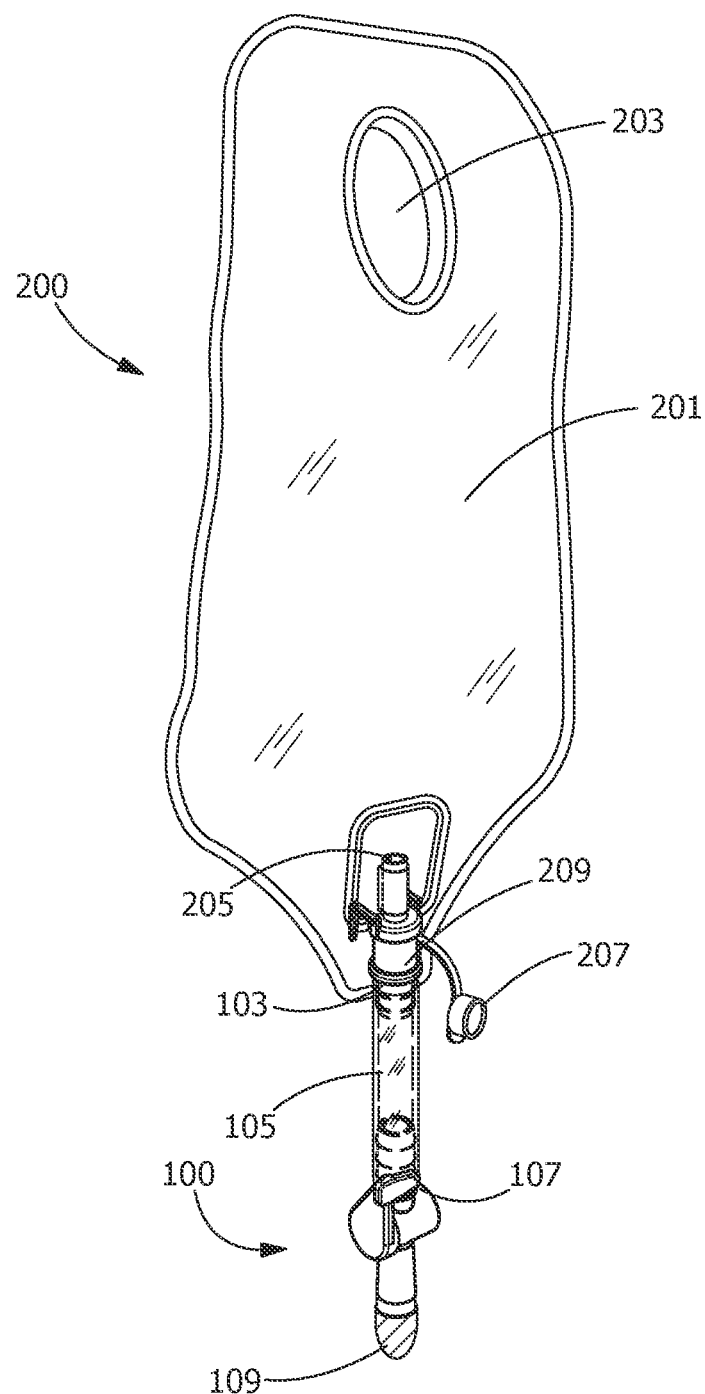
FIG. 2 schematically illustrates an ostomy bag assembly utilizing a drain assembly according to an embodiment of the present disclosure.

FIGS. 1 and 2 show a drain assembly 100 (see FIG. 1) for use with an ostomy bag 201 and an ostomy bag arrangement 200 (see FIG. 2) according to an embodiment of the present disclosure. Drain assembly 100 includes a connector 103 configured to attach to the ostomy bag 201. Connector 103 detachably engages an ostomy bag 201. Connector 103 may include features, such at hooks, detents, threading, clips, fasteners, or any other connecting features that allow the connector to detachably engage the ostomy bag 201. In certain embodiments, the connector 103 may be a connector commercially available form the ostomy bag manufacturer for connection to other ostomy bag accessories, such as connections to night bags. A flexible conduit 105 attaches to and extends from the connector 103. The flexible conduit 105 may be connected to connector 103 as a unitary component or may be attached by a suitable attachment mechanism, such as a hose barb or tapered connector. There are various configurations of connectors 103. One type of connector 103 connects by snapping onto a port found at the distal end of the drainage valve located at the bottom of an ostomy bag 201 or pouch. Other connectors 103 connect by pushing in the male end of a tapered cone into the drainage tube once the plug is removed. This type is used with bags which have no valve but use a tube with a plug. The drainage plug is pulled out and the cone is inserted. In one embodiment, connectors 103 have a configuration that may be used to connect a long tube, usually 4-6 feet, to drain opening of the ostomy bag 201 or pouch and at the distal end to connector to an overnight drainage collection system (not shown).

A discharge valve 107 is positioned at a distal end of the flexible conduit 105 from the connector 103. Like connector 103, the flexible conduit 105 may be attached to the discharge valve 107 by a suitable attachment mechanism, such as a hose barb or tapered connector, or the flexible conduit 105 and the discharge valve 107 may be a unitary component. The flexible conduit 105 is of a sufficient length and sufficient flexibility to permit an ostomy bag wearer 301 to position the discharge valve 107 into a discharge position outside of the ostomy bag wearer's 301 clothing for discharge of urine waste from the ostomy bag 201. Suitable lengths for the flexible conduit 105 include lengths or about 3 inches to about 8 inches. Alternately, the length of the drain assembly 100, including the flexible conduit 105, according to the present disclosure may be from 4 to 8 inches and may depend upon user preference. The length of the flexible conduit 105 is limited such that the length is sufficiently long to allow positioning of the discharge valve 107 into a location that permits drainage into a waste receptacle but is sufficiently short to avoid kinking or storage issues. In addition, if the total length of the drain assembly 100 is very short it is difficult and/or awkward to pull the drain assembly 100 through clothing to drain. If the drain assembly 100 is too short, the drain assembly 100 may slip into the underpants which may result in a requirement of the wearer to need to dig or reach for the drain assembly 100 inside their clothing. The length of the flexible conduit 105 serves to both allow convenient drainage of ostomy bag 201 and to permit the wearer to comfortably wear the ostomy bag arrangement 200. If the flexible conduit 105 is too long, the discharge valve 107 and the flexible conduit 105 may drop down the leg or lay against the genitals of the wearer.

Flexible conduit 105 may be fabricated from any suitable flexible material for contact with urine or other bodily fluids. For example, flexible conduit 105 may be a thermoplastic or fluoroplastic polymer, such as latex-free, vinyl tubing. Suitable materials for the flexible conduit 105 include, but are not limited to, polyethylene (PE), polyurethane (PU), polyvinylchloride (PVC), polytetrafluoroethylene (PTFE), fluorinated ethylene propylene (FEP) polyfluoroalkoxy alkane (PFA), polyvinylidene difluoride (PVDF), Polyether ether ketone (PEEK), silicone, nylon, Nalgene, thermoplastic elastomer (TPE) or any other suitable flexible tubing material. In addition to flexural modulus of the material of construction, the flexibility of the flexible conduit 105 is provided by the wall thickness. The diameter and the wall thickness of the flexible conduit 105 is a diameter suitable for draining of waster urine and flexible manipulation of the drain assembly 100. For example, in one embodiment, the diameter of the flexible conduit 105 may be from about 5 mm to about 15 mm, or from about 7 mm to about 13 mm, or from about 8 mm to about 10 mm or about 9 mm. Likewise, in one embodiment, the wall thickness may be from about 1.0 mm to about 2.0 mm or about 1.25 mm to about 1.75 mm or from about 1.4 mm to about 1.6 mm or about 1.5 mm. The flexibility of the material includes a flexural modulus that is sufficiently high or sufficiently stiff to maintain an open tube that allows flow of liquid, but also is sufficiently low or sufficiently flexible to permit movement and positioning of discharge valve 107. Further flexible conduit 105 is sufficiently flexible to avoid kinking and cutting off the flow of liquid. In addition, the flexible conduit 105 is sufficiently resilient to spring back to shape after being bent or compressed and/or sufficiently elastic to return to its shape quickly after being stretched or expanded. In addition, the flexible conduit 105 should have a hardness that is resistant to kinking at tight bends. Hardness of the flexible conduit 105 is measured as its durometer, and different scales, namely Shore A, Shore D, and Rockwell R, are commonly used for plastic and rubber materials. The lower the scale number, the softer and more flexible the material will be. For instance, a typical latex tubing hardness rating is Shore A35. Polyurethane tubing is not as soft and can measure between Shore A70 and A95. Harder materials like nylon and polyethylene are normally measured on the Shore D scale, and others (polypropylene, for example) use the Rockwell R scale. Flexibility may also be a function of hardness or durometer and wall thickness. In addition, the overall length of the flexible conduit 105 may also affect the flexibility. For example, a 6-inch-long flexible conduit 105 is more flexible than a 2½ inch flexible conduit. Lower durometer numbers are desired for the flexible conduit 105.

In one embodiment, the flexible conduit 105 may be formed from medical tubing commercially available from Thermo Fisher Scientific (Waltham, Massachusetts), Convatec (Reading, Berkshire, England, UK) or Saint Gobain Performance Plastics (La Défense, Courbevoie, France). A removable cap 109 may be optionally positioned on the discharge valve 107 to prevent undesired flow of urine from the discharge valve 107. Cap 109 may include a tether or similar retention feature to retain the cap 109 near the discharge valve 107 and prevent loss or dropping of the cap 109, for example in a urinal or toilet. In another embodiment, the flexible conduit 105 is a flexible corrugated tube to make it easier to bend from the bottom of the ostomy bag 201 to the zipper opening without bending or twisting the bag.

FIG. 2 shows an ostomy bag arrangement 200 according to an embodiment of the present disclosure. The ostomy bag arrangement 200 includes an ostomy bag 201 that is configured to receive waste urine from a person having a urostomy or other similar medical procedure that results in redirection of urine from the kidneys to a bag or reservoir outside of the body. "Ostomy bag", as utilized herein refers to bags or pouches utilized to collect urine. The terms ostomy "bag" and "pouch" are utilized interchangeably herein. For example, an ostomy bag wearer 301 may have had a urostomy. A urostomy is a surgery that creates a stoma in the patient's abdomen. Specifically, the stoma is attached to a place in the urinary tract to let urine leave the body. The majority of urostomies are placed on the right side and can be above the level of the umbilicus or below. At the stoma, the ostomy bag 201 may be attached or otherwise positioned on the wearer to collect urine for disposal. There are a number of configurations of ostomy bags 201, which are available from a number of different manufacturers. These ostomy bags 201 include an inlet opening 203 on a side of the ostomy bag 201 to receive urine from the stoma and a drain opening 205 at an end of the ostomy bag 201 that permits draining of the waste urine from the ostomy bag 201. As shown in FIG. 2, the ostomy bag 201 may include valve at the drain opening 205 to control the unintended flow of urine from the bag. While FIG. 2 shows this valve, the valve may be omitted and a cap 109, pin, pinched connection or other flow restraining features may be included. As shown in FIG. 2, a drain cap 207 in addition to the valve may be utilized to prevent the unintentional flow of urine.

The drain assembly 100 may attach to any ostomy bag 201, regardless of configuration or manufacturer, by configuring connector 103 to match the particular ostomy bag 201 discharge. The connector 103 detachably engages with a mating feature 209 of the ostomy bag 201. The mating feature 209 may include any suitable features, including barbs, tapers, threading, clips, protrusions, or other connecting features that detachable engage connector 103 and prevent leakage of liquid. These features may vary, for example, based upon manufacturer or ostomy bag configuration. For example, ostomy bags 201 are available from various manufacturers including Hollister (Libertyville, Illinois), Convatec (Reading, England, United Kingdom) and Coloplast (Humlebaek, Denmark). Connectors 103 that mate with the mating feature of 209 of these manufacturers may be of different diameters and configurations. The connectors 103, however, are integral to or connect to flexible conduit 105 of the drain assembly 100 according to an embodiment of the present disclosure. For example, connector 103 may include a hose barb or other connection suitable for connecting to the flexible conduit 105. The mating feature 209 and the connector 103 are detachable so that the drain assembly 100 may easily be removed from the ostomy bag 201 for either attachment to an ostomy bag accessory, such as a night receptacle, or so that the bag has a lower profile for the wearer for extended wear periods.

Figure 3:
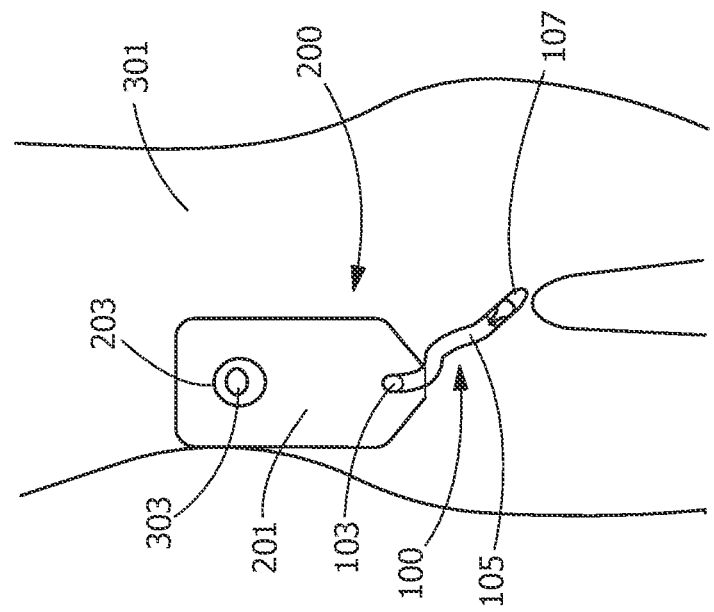
FIG. 3 schematically illustrates an ostomy bag wearer having an ostomy bag assembly utilizing a drain assembly according to an embodiment of the present disclosure.
Figure 4:
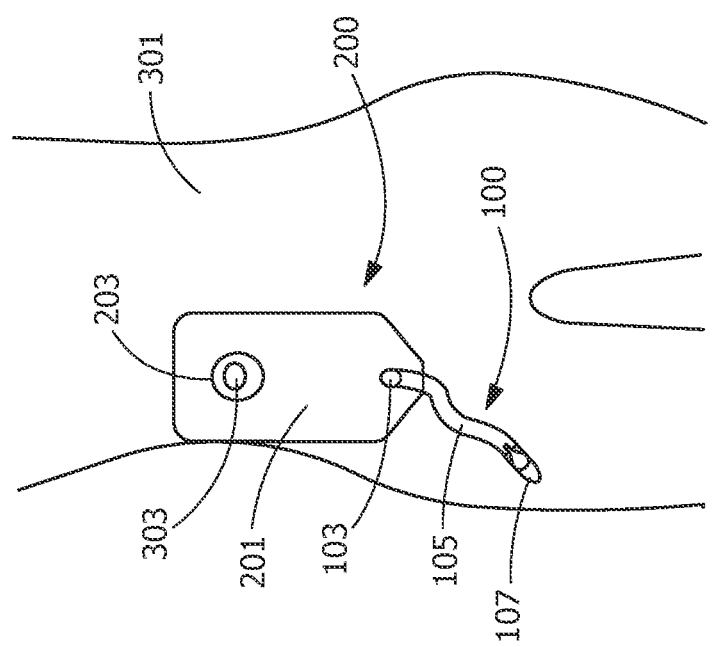
FIG. 4 shows the ostomy bag wearer of FIG. 3 with the drain assembly according to an embodiment of the present disclosure in an alternate position.

FIG. 3 shows an ostomy bag wearer 301 having a stoma 303 onto which an ostomy bag 201 is mounted. Ostomy bag 201 is part of an ostomy bag arrangement 201 according to the present disclosure. As shown in FIG. 2, the ostomy bag arrangement 200 includes a drain assembly 100 having a connector 103 that is attached to the ostomy bag 201. The connector 103 is likewise attached to a flexible conduit 105 that extends to a discharge valve 107. FIG. 4 includes the ostomy bag arrangement 200 as shown and described in FIG. 3, wherein the flexible conduit 105 and discharge valve 107 are in an alternate position. The use of the flexible conduit 105 in the drain assembly 100 allows such positioning. The positioning of the discharge valve 107 and the flexible conduit 105 is not limited to the positioning shown in FIGS. 3-5, but may include any positioning or storage within the reach provided by the flexible conduit 105. For example, the discharge valve 107 may be positioned or tucked into a pocket or waistband of the wearer's clothing 501. In another embodiment, the flexible conduit 105 allows for the ostomy bag arrangement 200 to be worn with the distal end including the discharge valve 107 at least partially sticking out or through an opening in undergarments, hidden from view by the clothing 501 of the wearer. The flexible positioning of the discharge valve 107 and the flexible conduit 105 permit discreet and convenient storage and positioning of the discharge valve 107 and flexible conduit 105 in the clothing of the ostomy bag wearer 301.

Figure 5:
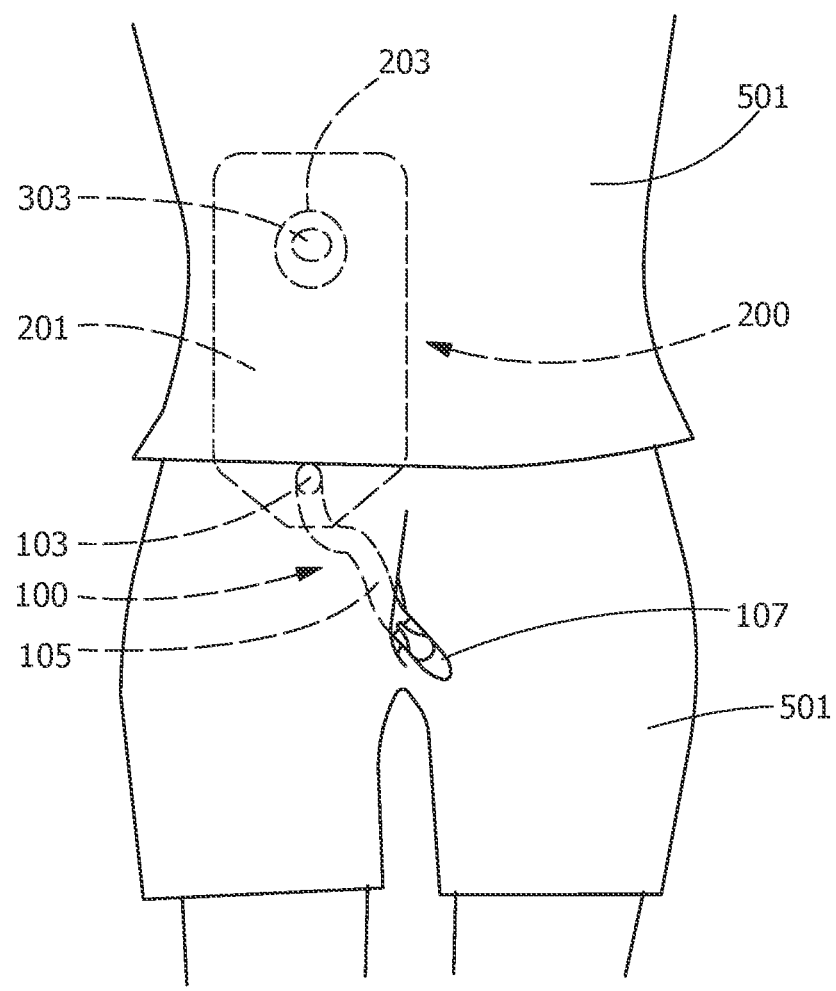
FIG. 5 shows an ostomy bag wearer of FIG. 3 directing a portion of the drain assembly according to the present disclosure through the wearer's clothing.

FIG. 5 shows an embodiment according to the present disclosure wherein the discharge valve 107 has been directed through an opening in the ostomy bag wearer's clothing 501 to permit drainage of the ostomy bag 201 into an external waste receptacle, such as a urinal or toilet. The positioning of the discharge valve 107 is not limited to the positioning shown in FIG. 5 and may include positioning over a waistband of the wearer's clothing 501, down underneath a wearer's skirt or shorts or through other openings in the wearer's clothing 501.

Figure 6:
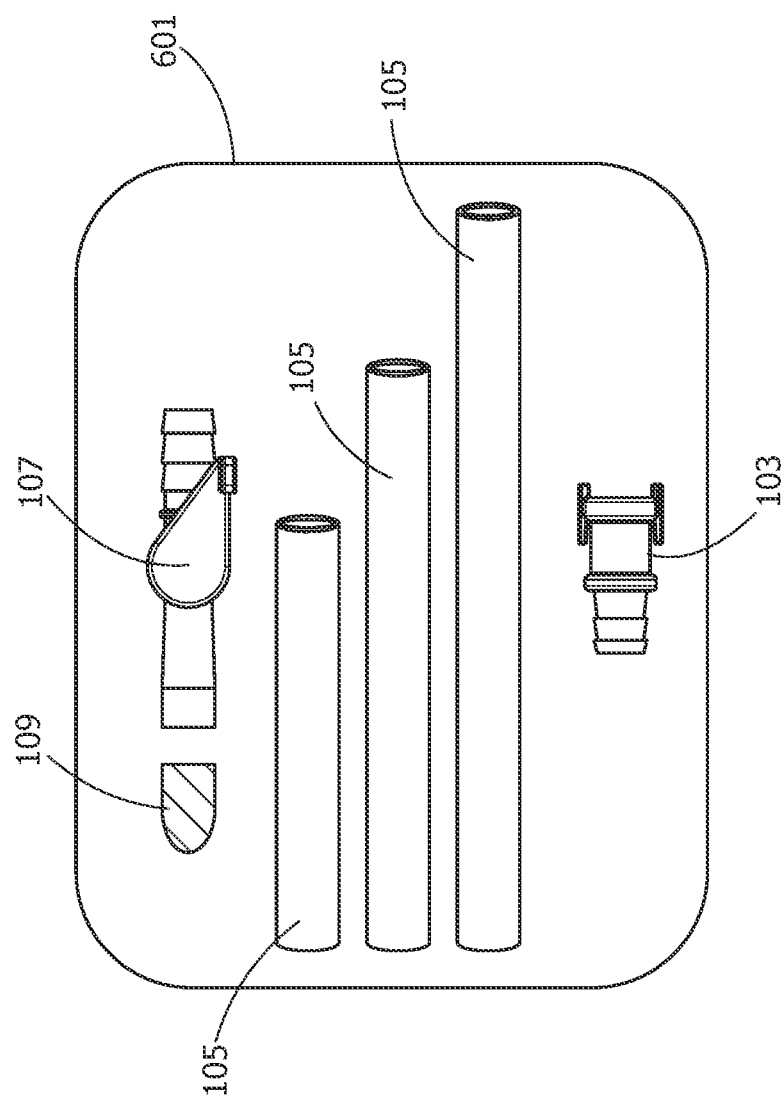
FIG. 6 shows a kit for assembly of a drain assembly for attachment to an ostomy bag according to an embodiment of the present disclosure.

FIG. 6 shows a kit 601 for assembly of a drain assembly 100 for attachment to an ostomy bag 201 according to an embodiment of the present disclosure. The kit 601 includes a plurality of flexible conduits 105 of different lengths, each having a configuration that permits attachment to a connector 103 and a discharge valve 107 at distal ends of the flexible conduit 105. FIG. 6 shows three flexible conduits 105, but the invention is not so limited. Any number of flexible conduits 105, such as more or less than three, may be provided in kit 601. For example, in one embodiment, flexible conduit lengths in a kit be categorized into short, medium, long and extra-long, depending on the comfort of the bag wearer 301. For example, suitable sizes of flexible conduit 105 may be provided in kit 601 to provide drain assembly 100 total lengths of the following: short—7.62 cm (3 in.), medium—10.16 cm (4 in.), long—15.24 cm (6 in) and extra-long—20.32 cm (8 in). In other embodiments, color coding or other indicia or a set of multiple lengths may be provided. The connector 103 is configured to attach to a mating feature 209 of an ostomy bag 201, which would be provided separately from kit 601. In another embodiment, kit 601 may include an ostomy bag 201 with a mating feature 209 to detachably engage the connector 103 of the drain assembly 100. Each of the connector 103 and the discharge valve 107 include connection features, such as hose barbs or tapered connectors to allow assembly of the flexible conduit 105 to each of the connector 103 and the discharge valve 107. The discharge valve 107 is configured to permit connection to the flexible conduit 105 at a distal end from the connector 103. Kit 601 may also include a cap 109. The cap 109 may be positioned on the discharge valve 107 to prevent undesired flow of urine from the discharge valve 107. Cap 109 may include a tether or similar feature to retain the cap 109 near the discharge valve 107 and prevent loss or dropping of the cap 109, for example in a urinal or toilet. The flexible conduit 105, when assembled to the connector 103 and the discharge valve 107, includes sufficient length and sufficient flexibility to permit an ostomy bag wearer 301 to position the discharge valve 107 into a discharge position outside of the ostomy bag wearer's clothing 501 for discharge of urine waste from the ostomy bag 201. The kit 601 may be contained in or includes a sealable container. In another embodiment, kit 601 may include a bag or carrying receptacle, to carry or store the components of the drain assembly 100 or to carry or store an assembly drain assembly 100. In this embodiment, the bag or carrying receptacle is preferably sealable to contain any odor or residual liquid.

To utilize the drain ostomy bag arrangement 200 according to the present disclosure, the wearer of the ostomy bag arrangement 200 positions themselves near a waste receptacle. For example, the wearer stands at a urinal or sits on a toilet. The wearer then directs the discharge valve 107 of the ostomy bag arrangement 200 to a position that allows direct flow of the waste urine from the ostomy bag 201 into the waste receptacle. The positioning of the discharge valve 107 is permitted by the flexible conduit 105. In another embodiment, particularly relevant for a female wearer, the wearer may stand facing a toilet to direct the discharge valve 107 toward the toilet. In this embodiment it may be desirable to have a longer flexible conduit 105, including, for example an 8 inch or more flexible conduit. In another embodiment, drain assembly 100 may include a bag or carrying receptacle, to carry or store the assembly drain assembly 100. In this embodiment, the bag or carrying receptacle is preferably sealable to contain any odor or residual liquid. In this embodiment, the wearer would remove the drain assembly 100 from the bag or carrying receptacle, connect the drain assembly 100 to the ostomy bag 201 and, upon completion of the draining, return the drain assembly 100 to the bag or carrying receptacle.

FIGS. 7-12 shows various configurations of discharge valves 107 suitable for use with the drain assembly 100 according to the present disclosure. Each of the discharge valves 107 includes a valve actuator 701 to actuate the valve between a closed position to an open position. In addition, discharge valves 107 include a valve body 703 connected to the valve actuator 701. The valve actuator 701 may be side, top mounted or otherwise mounted in a manner to permit actuation of the valve body 703. For example, the valve body 703 may include an internal cylinder where the valve actuator 701 actuates the cylinder a quarter turn to actuate the valve from an open position to close position. This actuation positions the bore of the valve body 703 to align itself longitudinally allowing fluid flow. The valve actuator 701 may be moved up, down or side to side or rotated for the quarter turn alignment. While the above has been described as a quarter turn actuation, greater or less than a quarter turn actuation may be used. In addition, the discharge valve 107 includes a discharge end 705 that permits discharge of urine from the drain assembly 100. The discharge end 705 includes a geometry that permits directing of the flow of waste urine into the desired waste receptacle. In addition, discharge end 705 has a geometry that permits the addition of a cap 109 (see FIGS. 1 and 2) to prevent the undesired flow of urine from the discharge valve 107. The discharge valve 107 further includes a discharge valve connector 707 that connects to flexible conduit 105 (flexible conduit 105 shown in FIGS. 7-9). The discharge valve connector 707 includes a hose barb, taper, protrusion or other feature that allows connection to flexible conduit 105. FIGS. 7-12 show various configurations of discharge valve connectors 707. In another embodiment, the discharge valves 107 may include a smooth low profile valve actuator 701 that would minimize edges and overall dimensions. This exemplary configuration provides mitigation against catching on the wearer's clothing 501. Other configurations of discharge valve 107 may be utilized with the drain assembly 100 according to the present disclosure.

While the exemplary embodiments illustrated in the figures and described herein are presently preferred, it should be understood that these embodiments are offered by way of example only. Accordingly, the present application is not limited to a particular embodiment but extends to various modifications that nevertheless fall within the scope of the appended claims. The order or sequence of any processes or method steps may be varied or re-sequenced according to alternative embodiments.

It is important to note that the construction and arrangement of the various exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited in the claims. For example, elements shown as integrally formed may be constructed of multiple parts or elements, the position of elements may be reversed or otherwise varied, and the nature or number of discrete elements or positions may be altered or varied. Accordingly, all such modifications are intended to be included within the scope of the present application. The order or sequence of any process or method steps may be varied or re-sequenced according to alternative embodiments. In the claims, any means-plus-function clause is intended to cover the structures described herein as performing the recited function and not only structural equivalents but also equivalent structures. Other substitutions, modifications, changes and omissions may be made in the design, operating conditions and arrangement of the exemplary embodiments without departing from the scope of the present application.

I claim:

1. A drain assembly for attachment to an ostomy bag, the drain assembly comprising:
    a connector configured to attach to the ostomy bag; and
    a discharge valve having discharge end having a geometry that permits the addition of a cap at a distal end of the discharge valve from the connector, the discharge valve being a low-profile valve with a valve actuator, the valve actuator being actuatable between a closed position and an open position to discharge urine waste from the ostomy bag;
    wherein the discharge valve and discharge end are positionable into a discharge position outside of the ostomy bag wearer's clothing for discharge of urine waste from the ostomy bag.

2. The drain assembly of claim 1, wherein the drain assembly includes the cap, the cap being arranged and disposed to cover the discharge end.

3. The drain assembly of claim 1, wherein the connector and discharge valve are a unitary component.

4. The drain assembly of claim 1, wherein the discharge valve includes an elongated geometry to provide an easy maneuvering of the discharge valve.

5. The drain assembly of claim 1, wherein the valve actuator is actuatable with an up and down movement.

6. The drain assembly according to claim 1, wherein the valve body includes an internal cylinder that is rotatably actuatable with the valve actuator from the closed position to the open position to allow fluid flow.

7. The drain assembly of claim 6, wherein the valve actuator is actuatable with an up and down movement.

8. The drain assembly of claim 6, wherein the valve actuator is a rotary valve actuator.

9. The drain assembly of claim 6, wherein the internal cylinder aligns the bore longitudinally in the open position to allow fluid flow.

10. An ostomy bag arrangement for elimination of waste urine from an ostomy bag comprising:
    an ostomy bag for receiving waste urine from an ostomy bag wearer;
    a drain assembly detachably engaged to the ostomy bag, the drain assembly comprising:
    a connector configured to attach to the ostomy bag; and
    a discharge valve having discharge end having a geometry that permits the addition of a cap at a distal end of the discharge valve from the connector, the discharge valve being a low-profile valve with a valve actuator, the valve actuator being actuatable between a closed position and an open position to discharge urine waste from the ostomy bag;
    wherein the discharge valve and discharge end are positionable into a discharge position outside of the ostomy bag wearer's clothing for discharge of urine waste from the ostomy bag.

11. The ostomy bag arrangement of claim 10, wherein the drain assembly includes the cap, the cap being arranged and disposed to cover the discharge end.

12. The ostomy bag arrangement of claim 10, wherein the connector, and discharge valve are a unitary piece.

13. The ostomy bag arrangement of claim 10, wherein the discharge valve includes an elongated geometry to provide an easy maneuvering of the discharge valve.

14. The ostomy bag arrangement of claim 10, wherein the valve actuator is a rotary valve actuator.

15. The ostomy bag arrangement of claim 10, wherein the valve actuator is actuatable with an up and down movement.

16. An ostomy bag arrangement for elimination of waste urine from an ostomy bag comprising:
    an ostomy bag for receiving waste urine from an ostomy bag wearer;
    a drain assembly detachably engaged to the ostomy bag, the drain assembly comprising:
    a connector configured to attach to the ostomy bag; and
    a discharge valve at a distal end from the connector, the discharge valve is a low-profile valve having a valve body, the valve body having an internal cylinder that is rotatably actuatable with a valve actuator from a closed position to an open position to allow fluid flow;
    wherein the drain assembly is configured to permit an ostomy bag wearer to position the valve into a discharge position and actuate the discharge valve outside of the ostomy bag wearer's clothing for discharge of urine waste from the ostomy bag.

17. The ostomy bag arrangement of claim 16, wherein the drain assembly includes a cap arranged and disposed to cover an outlet of the discharge valve.

18. The ostomy bag arrangement of claim 16, wherein the connector, and discharge valve are a unitary piece.

19. The ostomy bag arrangement of claim 16, wherein the discharge valve includes an elongated geometry to provide an easy maneuvering of the discharge valve.

20. The ostomy bag arrangement of claim 16, wherein the internal cylinder aligns the bore longitudinally in the open position to allow fluid flow.

* * * * *